US006124234A

United States Patent [19]

Fetzer et al.

[11] Patent Number: 6,124,234

[45] Date of Patent: Sep. 26, 2000

[54] CATALYST WITH FINE-PARTICLE DISPERSION OF THE ACTIVE COMPONENT

[75] Inventors: Thomas Fetzer, Speyer; Wolfgang Buechele, Ludwigshafen; Matthias Irgang, Heidelberg; Bernhard Otto, Limburgerhof; Hermann Wistuba; Gert Buerger, both of Mannheim, all of Germany

[73] Assignee: BASF Aktiengesellschaft, Ludwigshafen, Germany

[21] Appl. No.: 08/845,557

[22] Filed: Apr. 25, 1997

Related U.S. Application Data

[63] Continuation of application No. 08/403,874, filed as application No. PCT/EP94/00083, Jan. 13, 1994.

[30] Foreign Application Priority Data

Jan. 21, 1993 [DE] Germany ............................ 43 01 469

[51] Int. Cl.[7] ............................ B01J 23/32; B01J 23/42; B01J 23/60

[52] U.S. Cl. .......................... 502/326; 502/324; 502/326; 502/329; 502/355

[58] Field of Search .................................... 502/324, 326, 502/329, 355

[56] References Cited

U.S. PATENT DOCUMENTS

| | | | |
|---|---|---|---|
| 3,931,053 | 1/1976 | Kazakov et al. | 252/466 |
| 3,948,808 | 4/1976 | Box, Jr. et al. | 252/462 |
| 4,456,703 | 6/1984 | Aldridge | 502/335 |

FOREIGN PATENT DOCUMENTS

| | | |
|---|---|---|
| 371037 | 1/1989 | European Pat. Off. . |
| 3717111 | 11/1987 | Germany . |

*Primary Examiner*—Richard Booth
*Assistant Examiner*—Alexander G. Ghyka
*Attorney, Agent, or Firm*—John H. Shurtleff

[57] ABSTRACT

Catalysts prepared by combining M—$Al_2O_4$ where M is an element of Group Ib, VIIb or VIII of the Periodic Table of the Elements with tin, lead, an element of group IIa or IIb of the Periodic Table of the Elements as oxide or salt or in elemental form and calcining at 300–1300° C. under 0.1–200 bar and the process for preparing them.

10 Claims, No Drawings

CATALYST WITH FINE-PARTICLE DISPERSION OF THE ACTIVE COMPONENT

This application is a continuation of prior application Ser. No. 08/403,874, filed Mar. 24, 1995 (abandoned), which is a 371 of PCT/EP94/00083, filed Jan. 13, 1994.

The present invention relates to catalysts with fine-particle dispersion of the active component and to a process for preparing these catalysts.

WO-A-89/00082 and the citations given therein describe the preparation of oxide catalysts which contain Cu, Zn and Al, employing as precursor a Cu-An-Al alloy which is partly or completely converted into the oxide in an oxidation step. The catalysts are employed for preparing methanol.

DE-A-37 17 111 discloses a process for preparing a copper-containing catalyst for low-temperature shift conversion which, besides copper oxide, also contains zinc oxide and aluminum oxide. The catalyst is prepared by precipitation of the water-soluble salts from aqueous solution using an alkaline precipitant.

The known catalysts are unsatisfactory in respect of useful life and activity.

It is an object of the present invention to remedy the abovementioned disadvantages.

We have found that this object is achieved by novel and improved catalysts prepared by combining $M—Al_2O_4$ where M is an element of Group Ib, VIIb or VIII of the Periodic Table of the Elements with tin, lead, an element of group IIa or IIb of the Periodic Table of the Elements as oxide or salt or in elemental form and calcining at 300–1300° C. under 0.1–200 bar.

The catalysts according to the invention can be prepared as follows:

The starting material may be a solid oxide which is wholly or partly, ie. 1–100%, preferably 10–90%, particularly preferably 20–70%, by weight, a spinel of the composition $M—Al_2O_4$ in an $Al_2O_3$ matrix, and this can be mixed with the same or higher concentration of tin, lead, an element of group IIa or IIb of the Periodic Table of the Elements, as oxide or salt or in elemental form, and calcined at 300–1300° C., preferably 500–1200° C., particularly preferably 600–1100° C., under 0.1–200 bar, preferably 0.5–10 bar, particularly preferably under atmospheric pressure.

The mixing can take place, for example, by spraying, mechanical mixing, stirring or kneading the ground solid of the composition $M—Al_2O_4$, preferably in $Al_2O_3$, particularly preferably in $\gamma$-$Al_2O_3$, or preferably by impregnating an unground solid of the composition $M—Al_2O_{41}$ preferably in $Al_2O_3$, particularly preferably in $\gamma$-$Al_2O_3$, with a solution of salts of tin, lead, an element of group IIa or IIb of the Periodic Table of the Elements.

The liberation of the element M in the form of the element or oxide, which as a rule leads to fine-particle dispersion, can be induced by replacing the element M in the spinel in the calcination step by tin, lead, an element of group IIa or IIb of the Periodic Table of the Elements, in the form of the element, oxide or salt-like compound when the resulting spinel is more thermodynamically stable than the original spinel $M—Al_2O_4$.

Suitable as metal M in the starting oxides $M—Al_2O_4$ are elements of group Ib, VIIb and VIII of the Periodic Table of the Elements in the +2 oxidation state, such as $Mn^{2+}$, $Fe^{2+}$, $Co^{2+}$, $Ni^{2+}$ and $Cu^{2+}$, especially $Ni^{2+}$ and $Cu^{2+}$ or mixtures thereof.

The elements of group IIa or IIb of the Periodic Table of the Elements can be used in the form of the metal, oxides or salt-like compounds. Examples of salt-like compounds are carbonates, hydroxides, carboxylates, halides and oxo anions such as nitrates, nitrites, sulfites, sulfates, phosphites, phosphates, pyrophosphates, halites, halates and basic carbonates, preferably carbonates, hydroxides, carboxylates, nitrates, nitrites, sulfates, phosphates and basic carbonates, particularly preferably carbonates, hydroxides, basic carbonates and nitrates, preferably in the +2 oxidation state such as $Zn^{2+}$, $Mg^{2+}$, $Ca^{2+}$, $Sr^{2+}$ and $Ba^{2+}$, especially $Zn^{2+}$ and $Mg^{2+}$ or mixtures thereof.

The preparation of the starting oxide of the composition $M—Al_2O_4$, preferably in the form of a spinel, is disclosed in, for example, WO-A-82/00820, SU-A-426 968, FR-A-2 655 878 and Rev. Chim. 20 (1969) 105–106. It proves advantageous to impregnate an $Al_2O_3$ carrier with a soluble compound such as a salt of the cation M, eg. a nitrite, nitrate, sulfite, sulfate, carbonate, hydroxide, carboxylate, halide, halite or halate, and subsequently to decompose the anion to the oxide thermally. Another possibility comprises mixing a compound such as a salt of the cation M with an oxygen-containing aluminum compound, eg. by drying or in suspension, especially by spray-drying, compacting the material, eg. by kneading, where appropriate by adding a suitable molding aid, molding by extrusion, drying and subsequently calcining to form the spinel. The calcination can be carried out at 300–1300° C., preferably 600–1000° C.

Doping of aluminum oxide carriers with a large surface area, ie. the formation of mixed oxides, increases the thermal stability of the carrier (eg. DE-A-34 03 328, DE-A-25 00 548, Appl. Catal. 7 (1983) 211–220, J. Catal. 127 (1991) 595–604). The foreign ions may additionally contribute to the catalytic activity of the catalyst. The following elements may be generally employed for the doping: alkali metals, rare earth metals, Sc, Ti, V, Cr, Y, Zr, B, Si, Ge, P, Bi. The degree of replacement of aluminum oxide can be, for example, 0.01–20w by weight.

The particle size of the oxide of the metal M in the unused catalyst is 1–200 nm, preferably 3–100 nm, particularly preferably 10–50 nm. The particle size can be determined, for example, by XRD (X-ray diffraction) or TEM (transmission electron microscopy).

The catalysts according to the invention contain mesopores of 2–20 nm and macropores of more than 20 nm and have BET surface areas of 1–350 $m^2/g$, preferably 10–200 $m^2/g$, particularly preferably 25–150 $m^2/g$, and porosity of 0.01–0.8 ml/g.

The catalysts according to the invention are suitable, for example, for CO conversion and for methanol synthesis.

EXAMPLES

Preparation of the catalyst

EXAMPLE 1

A mixture of 284 g of Puralox® SCF (from Condea), 166 g of Pural® SB (from Condea) and 100 g of CuO (from Merck) was kneaded with 20 ml of formic acid (dissolved in 140 ml of $H_2O$) for 0.75 h, extruded to 3 mm extrudates, dried and calcined at 800° C. for 4 h.

A $CuAl_2O_4$-containing solid with a BET surface area of 112 $m^2/g$ and a bimodal pore radius distribution with a diameter of 25%. of the pores being in the range 10–1 micrometers and of 65% of the pores being in the range 20–5 nanometers was obtained.

71.4 g of the $CuAl_2O_4$-containing solid (water uptake: 69.1%) were impregnated twice with 49 ml of an aqueous solution which contained nitric acid (pH 3) and 32.6 g of $Zn(NO_3)_2$ and then left at room temperature for one hour.

The impregnated carrier was dried to constant weight at 120° C. and finally calcined at 600° C. for 4 h.

A $ZnA1_20_4$-containing solid with a BET surface area of 82 $m^2$/g and an unchanged bimodal pore radius distribution was obtained with formation of CuO.

The size of the copper oxide crystallites was determined using X-rays and is 28 nm.

We claim:

1. A catalyst in which the active component is dispersed as fine particles, said catalyst being prepared by the steps which comprise:

admixing a solid oxide consisting at least partly of a spinel M—$Al_2O_4$ in an $Al_2O_3$ matrix, wherein M is the active component selected from the group consisting of the elements of Groups Ib, VIIb and VII of the Periodic Table of the Elements, with an additional spinel-forming metal component selected from the group consisting of zinc and magnesium, or mixtures thereof, in elemental form or as an oxide or salt, and subsequently calcining the resulting mixture at temperatures of 300–1300° C. and under pressures of 0.1–200 bar, whereby said active component M is liberated predominately as its oxide from the spinel by replacement with said additional spinel-forming metal component.

2. A catalyst as claimed in claim 1, wherein said active component M is selected from the group consisting of manganese, iron, cobalt, nickel and copper.

3. A catalyst as claimed in claim 1, wherein said additional spinel-forming component replacing M is zinc.

4. A catalyst as claimed in claim 1, wherein said active component M is selected from the group consisting of nickel, copper and mixtures thereof.

5. A process as claimed in claim 1, wherein the particle size of the active metal component as its oxide distributed in the catalyst during the calcination step ranges from 1 to 200 nm.

6. A process as claimed in claim 1, wherein the particle size of the active metal component as its oxide distributed in the catalyst during the calcination step ranges from 3 to 100 nm.

7. A process as claimed in claim 1, wherein the particle size of the active metal component as its oxide distributed in the catalyst during the calcination step ranges from 10 to 50 nm.

8. A process as claimed in claim 1, wherein the prepared catalyst contains mesopores of 2–20 nm and macropores of more than 20 nm and has a BET surface area of from 1–350 m2/g and a porosity of 0.01–0.8 ml/g.

9. A process as claimed in claim 8, wherein the prepared catalyst has a BET surface area of from 10–200 $m^2$/g.

10. A process as claimed in claim 8, wherein the prepared catalyst has a BET surface area of from 25–150 $m^2$/g.

* * * * *

UNITED STATES PATENT AND TRADEMARK OFFICE

CERTIFICATE OF CORRECTION

PATENT NO. : 6,124,234

DATED : September 26, 2000

INVENTOR(S) : Fetzer et al

It is certified that error appears in the above-identified patent and that said Letters Patent is hereby corrected as shown below:

In column 3, line 15 (at line 7 of claim 1): change "VII" to read --VIII--.

Signed and Sealed this

Twenty-ninth Day of May, 2001

Attest:

NICHOLAS P. GODICI

Attesting Officer

Acting Director of the United States Patent and Trademark Office